(12) United States Patent
Yang et al.

(10) Patent No.: US 10,011,543 B2
(45) Date of Patent: Jul. 3, 2018

(54) METHOD TO IMPROVE HALOGENATION REACTIONS

(71) Applicant: Honeywell International Inc., Morris Plains, NJ (US)

(72) Inventors: Terris Yang, East Amherst, NY (US); Hsueh Sung Tung, Getzville, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/214,615

(22) Filed: Jul. 20, 2016

(65) Prior Publication Data

US 2016/0326072 A1 Nov. 10, 2016

Related U.S. Application Data

(63) Continuation of application No. 14/873,346, filed on Oct. 2, 2015, now Pat. No. 9,416,073.

(60) Provisional application No. 62/060,272, filed on Oct. 6, 2014.

(51) Int. Cl.
| | |
|---|---|
| *C07C 17/02* | (2006.01) |
| *C07C 17/04* | (2006.01) |
| *C07C 17/013* | (2006.01) |
| *B01J 19/24* | (2006.01) |
| *B01J 19/30* | (2006.01) |

(52) U.S. Cl.
CPC ............ *C07C 17/04* (2013.01); *B01J 19/245* (2013.01); *B01J 19/30* (2013.01); *C07C 17/013* (2013.01); *B01J 2219/24* (2013.01); *B01J 2219/30408* (2013.01); *B01J 2219/30466* (2013.01); *C07C 17/02* (2013.01)

(58) Field of Classification Search
CPC ....................................................... C07C 17/02
See application file for complete search history.

(56) References Cited

U.S. PATENT DOCUMENTS 4,072,728 A * 2/1978 Costes .................... C07C 17/02
570/247
4,548,995 A 10/1985 Kowalski et al.
(Continued)

FOREIGN PATENT DOCUMENTS

| CN | 104058928 A | 9/2014 |
|---|---|---|
| EP | 1396505 A1 | 3/2004 |
| WO | 2013015068 A1 | 1/2013 |

OTHER PUBLICATIONS

NPL 1, "Temperature Control of a Plug Flow Reactor", Oct. 8, 2009, pp. 1-2.*

(Continued)

*Primary Examiner* — Medhanit W Bahta
(74) *Attorney, Agent, or Firm* — Bruce O. Bradford

(57) ABSTRACT

In the halogenation reaction of organic olefin compounds, an excess amount of halogen gas (fluorine, chlorine, vaporized bromine and iodine, or their combination) is normally used in order to achieve as complete as possible conversion of the organic starting material. In a conventional process, the excess halogen gas in the off-gas stream is scrubbed by caustic solution which increases the consumption of halogen and generates waste for disposal. The present invention provides a novel process to recover and reuse the excess halogen gas and thus reduce the operating cost of the process.

10 Claims, 1 Drawing Sheet

Novel Process

(56) References Cited

U.S. PATENT DOCUMENTS

| | | | |
|---|---|---|---|
| 6,235,953 B1 * | 5/2001 | Schwarzmaier | B01J 10/002 422/198 |
| 8,415,512 B2 | 4/2013 | Sherman et al. | |
| 2003/0049485 A1 * | 3/2003 | Brupbacher | B05D 5/083 428/615 |

OTHER PUBLICATIONS

Hauffe, K. et al. Soc. Chem. Eng. Biotech., Jan. 31, 2011, pp. 1-8.*

* cited by examiner

Figure 1 – Prior Art
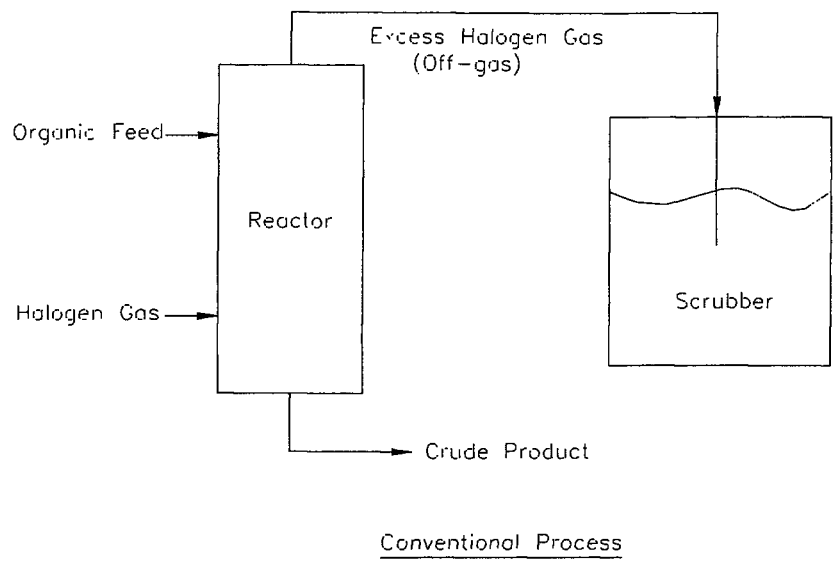
Conventional Process
Figure 2
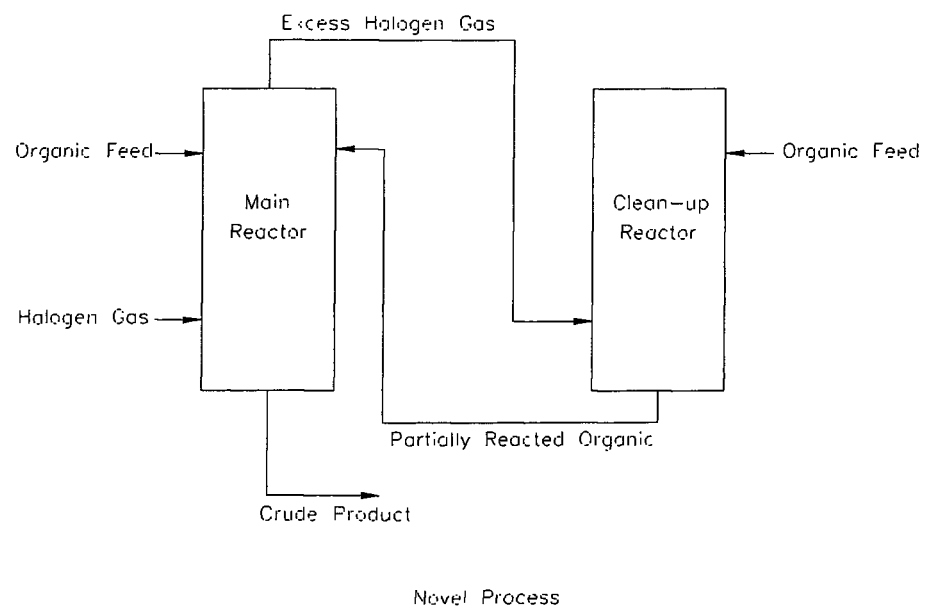
Novel Process

METHOD TO IMPROVE HALOGENATION REACTIONS

CROSS-REFERENCE TO RELATED APPLICATIONS

This application is a continuation of commonly owned, copending U.S. patent application Ser. No. 14/873,346, filed Oct. 2, 2015, now U.S. Pat. No. 9,416,073. The '346 Application claims domestic priority from commonly owned, U.S. Provisional Patent Application Ser. No. 62/060,272, filed 6 Oct. 2014. The disclosures of these applications are hereby incorporated herein by reference.

BACKGROUND OF THE INVENTION

In typical halogenation reactions of olefin or halo-olefin compounds (i.e., organic), an excess amount of halogen gas (fluorine, chlorine, bromine, iodine, or their combinations) is normally used in order to achieve maximum halogenation of the organic. In a conventional halogenation process, one reactor is used and the excess halogen gas in the off-gas stream is scrubbed by a caustic solution. This increases the consumption of halogen and generates waste for later disposal. The present invention is directed to a novel process which permits recovery of the excess halogen gas, which thereby reduces the operating cost of the reaction.

SUMMARY OF THE INVENTION

The present invention is a novel process which permits recovery of the excess halogen gas, which thereby reduces the operating cost of the reaction. The process described herein makes use of two reactors instead of one, a main reactor and a "clean-up" reactor. The main reactor is used to conduct the halogenation reaction in a conventional manner. The clean-up reactor is charged with the same organic starting material as used in the main reactor.

During the operation of the main reactor an excess amount of halogen gas is fed into the main reactor and this reacts with the organic. Unreacted excess halogen gas in the off-gas stream is directed into the clean-up reactor and there the halogen gas is captured by the organic starting material held in the clean-up reactor. In order to fully remove the halogen gas, the amount of the organic in the clean-up reactor is in stoichiometric excess compared to the amount of halogen gas in the off-gas stream from the main reactor. The process can be operated in either batch or continuous mode.

In a batch operation, a fixed amount of organic is charged into both the main reactor and the clean-up reactor. Then, halogen gas is introduced into the main reactor until the designated amount of halogen gas is fed into the main reactor (normally, 1.1 to 1.5 times of halogen gas to organic molar ratio by stoichiometric). The excess amount of halogen gas in the off-gas stream reacts with the organic in the clean-up reactor. The partially reacted organic in the clean-up reactor can be temporally stored and charged into the main reactor soon after as the starting material for next batch of operation.

In a continuous operation, the organic is charged into both the main reactor and the clean-up reactor. The main reactor runs in batch mode to prepare for the continuous operation. After the main reactor is well batched, halogen gas and the organic are continuous fed into the main reactor with halogen gas in excess (normally, 1.1 to 1.5 times of halogen gas to organic molar ratio by stoichiometric). At the same time, fresh organic is also fed into the clean-up reactor continuously or periodically. The excess amount of halogen gas in the off-gas stream reacts with the organic in the clean-up reactor. The partially reacted organic from the clean-up reactor is continuously or periodically discharged from the clean-up reactor and fed into the main reactor to further react with the halogen gas.

Both main reactor and clean-up reactor can be continuous stirred tank reactors (CSTR) and/or plug flow reactors, or any other suitable type of reactor for halogenation reactions. Both of the reactors can be either empty or packed with any halogen-resistant material to assist with the reaction. In some embodiments, the packing material comprises Stainless Steel, Inconel, Monel, other metal alloys, and the like. In some embodiments, the packing material comprises fluorocarbon plastics, such as PFA, PTFE, and the like.

As an example, this process can be used in the chlorination of 1,1,3-trichloropropene (HCC-1240za) to make 1,1,1,2,3-pentachloropropane (HCC-240db).

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

BRIEF DESCRIPTION OF THE DRAWINGS

FIG. 1 shows a convention halogenation reactor system, employing one reactor and a scrubber to handle excess halogen.

FIG. 2 shows an embodiment of the halogenation reactor system of the present invention, employing one main reactor and a second clean-up reactor.

DETAILED DESCRIPTION OF THE INVENTION

As shown in FIG. 2, the present invention introduces a second reactor (a clean-up reactor) into the process of halogenation reaction of olefin/halo-olefin, which can recover the excess halogen gas and reduce the operating cost. Both main reactor and clean-up reactor can be CSTR and/or plug flow reactors, or any other type of halogenation reactors. As an example, this process can be used in the chlorination of HCC-1240za to make HCC-240db.

The process can be operated in either batch or continuous mode. In a batch operation, a fixed amount of organic is charged into both the main reactor and the clean-up reactor. Then, halogen gas is introduced into the main reactor until the designated amount of halogen gas is fed into the main reactor (normally, from 1.1 to 1.5 times of halogen gas to organic molar ratio by stoichiometry). The excess amount of halogen gas in the off-gas stream reacts with the organic in the clean-up reactor. The partially reacted organic in the clean-up reactor can be temporally stored and charged into the main reactor as the starting material for next batch operation.

In a continuous operation, the organic is charged into both the main reactor and the clean-up reactor. The main reactor runs in batch mode to prepare for the continuous operation. After the main reactor is well batched, halogen gas and the organic are continuous fed into the main reactor with halogen gas in excess (normally, 1.1 to 1.5 times of halogen gas to organic molar ratio by stoichiometry). At the same time, fresh organic is also fed into the clean-up reactor continuously or periodically. The excess amount of halogen gas in the off-gas stream reacts with the organic in the clean-up reactor. The partially reacted organic from the clean-up reactor is continuously or periodically discharged from the clean-up reactor and fed into the main reactor to further react with the halogen gas.

Example 1: HCC-240db Synthesis—Batch Operation

A 500 ml main reactor equipped with a $Cl_2$ gas sparger and a total condenser is charged with 250 g of 1,1,3-trichloropropene (99.5 wt % pure). The reactor is stirred and heated using an oil bath which has been preheated to 80° C. After the reactor temperature reaches 80° C., $Cl_2$ gas is fed into the reactor via the gas sparger. The reactor temperature is controlled at 80° C.±5° C. by controlling the feed rate of $Cl_2$ gas and adjusting the oil bath temperature setting. During the operation, the total $Cl_2$ feed is maintained at 110-120 mol % of 1,1,3-trichloropropene charged into the reactor, and HCC-240db is removed as crude product for further purification.

Excess $Cl_2$ gas from the main reactor is fed to a clean-up reactor containing 250 g of 1,1,3-trichloropropene (99.5 wt % pure) thereby forming additional crude HCC-240db, which is recycled to the main reactor.

Example 2: HCC-240db Synthesis—Continuous Operation

A 500 ml main reactor and a 500 ml clean-up reactor both equipped with a $Cl_2$ gas sparger and a total condenser are charged with 250 g of 1,1,3-trichloropropene (99.5 wt % pure), respectively. Both reactors are stirred and heated using oil baths which have been preheated to 80° C.

After both reactor temperatures reach 80° C., $Cl_2$ gas is fed into the main reactor via the gas sparger. The reactor temperature is controlled at 80° C.±5° C. by controlling the feed rate of $Cl_2$ gas and adjusting the oil bath temperature setting. The off-gas from the main reactor is fed into the clean-up reactor via the sparger. After about 140 g of $Cl_2$ is fed into the main reactor, the continuous operation is started by feeding fresh 1,1,3-trichloropropene into the clean-up reactor at about 125 g/h, $Cl_2$ into the main reactor at about 135 g/h, and drawing off HCC-240db from the main reactor at about 186 g/h. The organic in the clean-up reactor is continuously transferred to the main reactor at an appropriate rate which maintains stable level in both reactors.

Example 3: HCC-240db Synthesis—Continuous Operation

A 500 ml main reactor and a 500 ml clean-up reactor both equipped with a $Cl_2$ gas sparger and a total condenser are charged with 372 g of HCC-240db (99.5 wt % pure) for the main reactor and 250 g of 1,1,3-trichloropropene (99.5 wt % pure) for the clean-up reactor, respectively. Both reactors are stirred and heated using oil baths which have been preheated to 80° C.

After both reactor temperatures reach 80° C., $Cl_2$ gas is continuously fed into the main reactor via the gas sparger at about 135 g/h, fresh 1,1,3-trichloropropene is continuously fed into the clean-up reactor at about 125 g/h, and HCC-240db is continuously drawn-off from the main reactor at about 186 g/h. At the same time, the organic in the clean-up reactor is continuously transferred to the main reactor at an appropriate rate which maintains stable level in both reactors. Both reactor temperatures are controlled at 80° C.±5° C. by adjusting the oil bath temperature setting.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for the halogenation of an organic starting material comprising an olefin compound comprising the steps of:
    (a) using a first reactor and conducting the halogenation of the organic starting material with a stoichiometric excess amount of halogen gas;
    (b) using a second reactor and conducting the halogenation of the organic starting material with the unreacted excess halogen gas from the first reactor with a stoichiometric excess amount of the organic starting material; and
    (c) returning the partially reacted organic starting material in the second reactor to the first reactor to react with a stoichiometric excess amount of halogen gas; wherein the partially reacted organic starting material in the second reactor is returned to the first reactor to react with a stoichiometric excess amount of halogen gas;
    wherein when the first reactor is a continuous stirred tank reactor (CSTR), the second reactor is a plug flow reactor; or when the first reactor is a plug flow reactor, the second reactor is a continuous stirred tank reactor (CSTR).

2. The process of claim 1, wherein the halogenation reaction is conducted in a batch mode.

3. The process of claim 1, wherein the halogenation reaction is conducted in a continuous mode.

4. The process of claim 1, wherein the halogen gas used in the process is selected from the group consisting of fluorine, chlorine, bromine, iodine, and combinations thereof.

5. The process of claim 1, wherein the reactors can be either empty or packed with a halogen-resistant material to assist with the reaction.

6. The process of claim 5, wherein at least one reactor includes a packing material.

7. The process of claim 6, wherein the packing material is selected from the group consisting of Stainless Steel, nickel-chromium alloys, nickel-copper alloys, and other metal alloys.

8. The process of claim 6, wherein the packing material comprises fluorocarbon plastics.

9. The process of claim 8, wherein the packing material comprises perfluoroalkoxy alkanes (PFA).

10. The process of claim 8, wherein the packing material comprises polytetrafluoroethylene (PTFE).

* * * * *